United States Patent [19]

Brown

[11] Patent Number: 5,069,757
[45] Date of Patent: Dec. 3, 1991

[54] SEPARATION OF AROMATICS FROM ALKANES

[75] Inventor: Ronald E. Brown, Bartlesville, Okla.

[73] Assignee: Phillips Petroleum Company, Bartlesville, Okla.

[21] Appl. No.: 547,553

[22] Filed: Jul. 2, 1990

[51] Int. Cl.$^5$ .............................................. B01D 3/40
[52] U.S. Cl. ........................................ 203/51; 203/58; 585/857; 585/860; 585/865
[58] Field of Search ................... 203/51, 52, 58, 68, 203/57, 191, 70, 69; 585/833, 857, 860, 867, 865, 800; 208/313

[56] References Cited

U.S. PATENT DOCUMENTS

| | | | |
|---|---|---|---|
| 2,891,894 | 6/1959 | Cier et al. | 203/60 |
| 3,114,783 | 12/1963 | Butler et al. | 203/55 |
| 3,591,490 | 7/1971 | Müller et al. | 208/313 |
| 3,723,256 | 3/1973 | Thompson | 203/43 |
| 4,053,369 | 10/1977 | Cines | 203/52 |
| 4,278,505 | 7/1981 | Danulat et al. | 203/59 |
| 4,401,517 | 8/1983 | Lee | 203/53 |
| 4,514,262 | 4/1985 | Berg | 203/51 |
| 4,690,733 | 9/1987 | Forte | 203/21 |
| 4,746,420 | 5/1988 | Darian et al. | 208/222 |
| 4,944,849 | 7/1990 | Lee | 203/55 |
| 4,948,470 | 8/1990 | Lee | 203/53 |
| 4,954,224 | 9/1990 | Brown et al. | 203/51 |
| 4,955,468 | 9/1990 | Lee | 203/53 |

OTHER PUBLICATIONS

"Perry's Chemical Engineers' Handbook", 6th Edition, by Robert H. Perry et al., 1984; pp. 13-53 to 13-57.
"Handbook of Separation Techniques for Chemical Engineers", by Philip A. Schweitzer, 1979; pp. 1-135 to 1-143.
"Extractive Distillation Saves Energy", by I. Sucksmith, Chemical Engineering, Jun. 28, 1982, pp. 91-95.

Primary Examiner—Virginia Manoharan
Attorney, Agent, or Firm—K. K. Brandes

[57] ABSTRACT

An extractive distillation process for separating at least one aromatic hydrocarbon from at least one close-boiling alkane employs as solvent a mixture of (a) at least one N-mercaptoalkyl-2-pyrrolidone, preferably N-($\beta$-mercaptoethyl)-2-pyrrolidone and (b) at least one sulfolane, preferably cyclotetramethylene sulfone.

9 Claims, 1 Drawing Sheet

SEPARATION OF AROMATICS FROM ALKANES

BACKGROUND OF THE INVENTION

This invention relates to the separation of aromatic hydrocarbons from close-boiling alkanes by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91-95. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company 1984, pages 13-53 to 13-57.

The separation of aromatics from non-aromatics, in particular alkanes, by extractive distillation is known and has been described in U.S. Pat. Nos. 3,591,490; 3,723,526; 4,053,369 and 4,278,505. However, there is an ever present need to develop more suitable solvents than those presently known in the extractive distillation of mixtures of aromatic and non-aromatic hydrocarbons.

SUMMARY OF THE INVENTION

It is an object of this invention to provide a process for separating aromatic hydrocarbons from close-boiling alkanes by extractive distillation employing a novel solvent mixture (also referred to as extractant or entrainer). Other objects and advantages will be apparent from the detailed description of the invention and the appended claims.

In accordance with this invention, in a process for separating at least one aromatic hydrocarbon containing 6-10 carbon atoms per molecule from at least one close-boiling alkane by extractive distillation of a feed comprising (preferably consisting essentially of) said at least one aromatic hydrocarbon and said at least one close-boiling alkanes, the improvement comprises employing a solvent consisting essentially of a mixture of (a) at least one N-mercaptoalkyl-2-pyrrolidone, wherein the mercaptoalkyl group contains 1-5 carbon atoms, and (b) at least one sulfolane compound containing 4-8 carbon atoms per molecule.

DETAILED DESCRIPTION OF THE INVENTION

Figure 1:
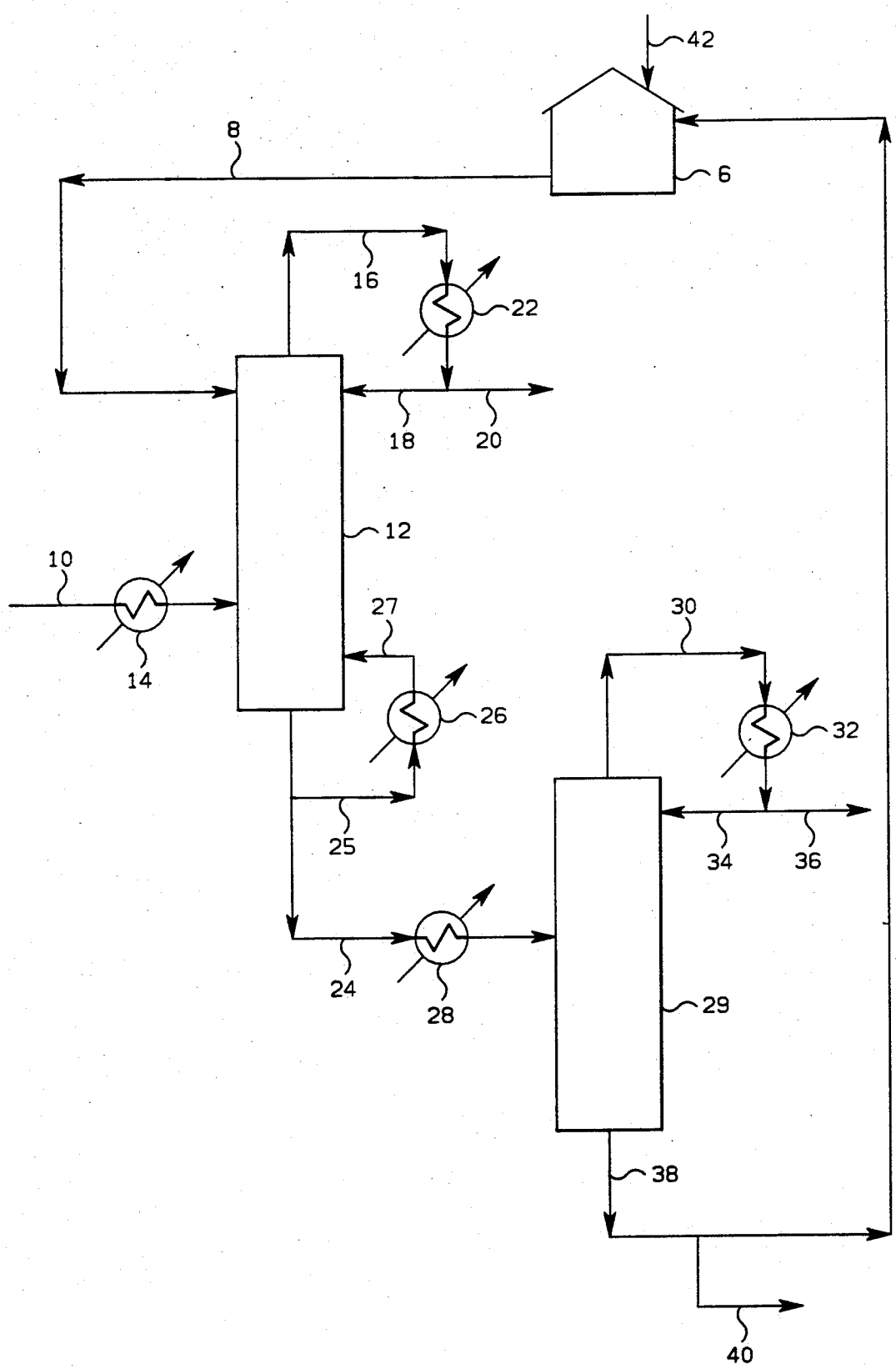
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative voltilities of the components in a mixture, and will allow for the separation of components in a mixture with fewer distillation stages, lower amount of reflux and higher product purity. The term "close-boiling" as used herein, means that the aromatic hydrocarbon(s) and the alkane(s) contained in the feed have nearly the same boiling point at atmospheric pressure.

In the process of this invention, any hydrocarbon feed which contains at least one aromatic hydrocarbon containing 6-10 carbon atoms per molecule and at least one close-boiling alkane (preferably containing 5-10 carbon atoms per molecule) can be used in the extractive distillation process of this invention. Preferably, the boiling points (at atmospheric pressure conditions, i.e., at about 1 atm.) of the aromatic hydrocarbon(s) and of the alkane(s) to be separated by extractive distillation process of this invention, are in the range of from about 80° to about 350° F., more preferably about 100°-300° F. Generally, the boiling points of the aromatic hydrocarbon(s) and of the alkane(s) differ by about 0.2°-10° F. (preferably about 0.5°-5° F.), at about 1 atm.

Preferably, the aromatics content in the feed is about 10-95 weight-% (more preferably about 20-80 weight-%), and the alkane content is about 5-90 weight-% (more preferably about 20-80 weight-%).

Non-limiting examples of suitable feed alkanes are n-pentane, n-hexane, 2-methylpentane, 3-methylpentane, n-heptane, 2,2-dimethylpentane, 2,4-dimethylpentane, 3,3-dimethylpentane, 2,3-dimethylpentane, 2-methylhexane, 3-methylhexane, 2,2,3-trimethylbutane, n-octane, 2-methyloctane, n-nonane, and the like, and mixtures thereof, in particular n-heptane.

Non-limiting examples of suitable aromatic hydrocarbons are benzene, toluene, meta-, ortho- and para-xylenes, ethylbenzene, trimethylbenzenes, methylethylbenzenes, and the like, and mixtures of the above. Preferred aromatic hydrocarbons are benzene and toluene.

The general structural formula of N-mercaptoalkyl-2-pyrrolidones, which are useful as component (a) of the solvent and in the process of this invention, is

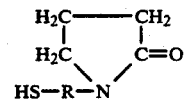

wherein R is a radical selected from the group consisting of —CH$_2$—, —CH$_2$—CH$_2$—, —CH$_2$—CH$_2$—CH$_2$—, —CH(CH$_3$)—CH$_2$—, —CH$_2$—CH(CH$_3$)—, —CH(CH$_3$)—CH(CH$_3$)—, —C(CH$_3$)$_2$—CH(CH$_3$)—, —CH$_2$—CH$_2$—CH$_2$—CH$_2$—, —CH$_2$—CH$_2$—CH$_2$—CH$_2$—CH$_2$—, and the like, and mixtures thereof. The preferred radical R is —CH$_2$—CH$_2$—. Thus, the preferred solvent is N-(β-mercaptoethyl)-2-pyrrolidone:

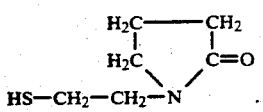

The N-(mercaptoalkyl)-2-pyrrolidones can be prepared by UV-catalyzed addition of H₂S to the corresponding N-alkenyl-2-pyrrolidone. For instance, N-(β-mercaptoethyl)-2-pyrrolidone is prepared by reaction of H₂S and N-vinyl-2-pyrrolidone, at room temperature (about 25° C.) and a molar ratio of H₂S to N-vinyl-2-pyrrolidone of about 5–6:1, while the reaction mixture is continuously stirred and subjected to UV radiation, for about 4–6 hours. The formed product, N-(β-mercaptoethyl)-2-pyrrolidone (boiling point: 266° C. at 1 atm; 100° C. at 0.3 mm Hg), is separated from unreacted N-vinylpyrrolidone by fractional distillation.

Non-limiting examples of sulfolanes (defined by Formula 1 in U.S. Pat. No. 4,053,369) which are suitable as component (b) of the solvent of this invention are unsubstituted sulfolane (also referred to as 2,3,4,5-tetrahydrothiophene-1,1-dioxide or cyclotetramethylene sulfone), 2-methylsulfolane, 3-methylsulfolane, 2,3-dimethylsulfolane, 2,4-dimethylsulfolane, 2-ethylsulfolane, 2,3,4,5-tetramethylsulfolane, and the like, and mixtures thereof. Presently preferred is cyclotetramethylene sulfone having the formula $(CH_2)_4SO_2$, as determined by Formula 4 in U.S. Pat. No. 4,053,369.

Any suitable weight ratio of component (b) to component (a) in the solvent (also called extractant or entrainer) can be employed in the extractive distillation process of this invention. Preferably, the weight ratio of component (b) to component (a) is in the range of from about 0.2:1 to about 30:1, more preferably from about 1:1 to about 10:1.

Any suitable weight ratio of the solvent to the hydrocarbon containing feed mixture can be employed. Preferably, the solvent to feed weight ratio is in the range of from about 0.5:1 to about 40:1, more preferably from about 1:1 to about 10:1.

Any suitable reflux ratio (i.e., the weight ratio of the portion of condensed vapor which is returned to the distillation column to the portion of condensed vapor which is withdrawn as distillate product) can be employed in the extractive distillation process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 100° to about 300° F., preferably in the range of from about 150° to about 250° F. Solvent and feed are generally preheated (generally to a temperature close to the column temperature of the corresponding entry point) before they are introduced into the column. Any suitable pressure can be employed during the extractive distillation. Generally the pressure is about 5 about 100 psig, preferably about 8 to about 20 psig.

The overhead distillate product (withdrawn from the top of the column) generally contains a smaller volume percentage of the aromatic hydrocarbon(s) than the feed and a larger volume percentage of alkane(s) than the feed. Generally, the bottoms product (a portion of which can be reheated and recycled to the lower portion of the column) contains more of the aromatic hydrocarbon(s) than the feed, and less of the alkane(s) than the feed. Furthermore, the bottoms product contains essentially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. The feed mixture comprising aromatic hydrocarbon(s) and close-boiling alkane(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in alkane(s) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12.

For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in alkane(s) and a bottoms stream predominantly comprising the aromatic hydrocarbon(s) and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising aromatic hydrocarbons is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., aromatic hydrocarbon(s) preferably benzene and/or toluene and/or xylenes) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE

This example demonstrates the superiority of a mixture of unsubstituted sulfolane (cyclotetramethylene sulfone; hereinafter referred to as "sulfolane") and N-(β-mercaptoethyl)-2-pyrrolidone (abbreviated NMEP) versus each component alone in the extractive distillation of an aromatics/alkane feed.

To a hydrocarbon mixture of 50 weight-% toluene and 50 weight-% n-heptane was added an extractive solvent (either sulfolane or NMEP or a mixture of 50 weight-% sulfolane and 50 weight-% NMEP) at various solvent: feed weight ratios. The total mixture (including the extractive solvent) was heated under reflux conditions for about 20–30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of toluene and n-heptane in the liquid phase and in the vapor phase were determined. The relative volatility R was calculated as follows:

$$R = \frac{Y1/Y2}{X2/X1} = \frac{Y1/X1}{Y2/X2},$$

wherein Y1 and Y2 are the mole fractions of toluene and n-heptane, respectively, in the vapor phase; and X1 and X2 are the mole fractions of toluene and n-heptane, respectively, in the liquid phase. Test results are summarized in Table I.

TABLE I

| Solvent:Feed Weight Ratio | Added Solvent | Relative Volatility R |
|---|---|---|
| 1:1 | Sulfolane | 2.10 |
| 1:1 | NMEP | 2.42 |
| 1:1 | Sulfolane + NMEP[1] | 2.49 |
| 3:1 | Sulfolane | 3.27 |
| 3:1 | NMEP | 3.12 |
| 3:1 | Sulfolane + NMEP[1] | 4.12 |
| 5:1 | Sulfolane | 4.51 |
| 5:1 | NMEP | 3.92 |
| 5:1 | Sulfolane + NMEP[1] | 5.69 |

[1]mixture of 50 weight-% sulfolane and 50 weight-% NMEP.

Based on the test results in Table I, it is concluded that mixtures of sulfolane and N-mercaptoalkyl-2-pyrrolidone (in particular NMEP) would be more effective than sulfolane alone or N-mercaptoalkyl-2-pyrrolidone (in particular NMEP) alone as solvent in the extractive distillation of feeds containing aromatics and close-boiling alkane(s). These test data also show that a solvent to feed weight ratio of 3:1 or higher would be a preferred operating parameter of the extractive distillation process.

Reasonable variations, modifications and adaptations for various usages and conditions can be made within the scope of the disclosure and the appended claims, without departing from the scope of this invention.

That which is claimed is:

1. In a process for separating at least one aromatic hydrocarbon containing 6–10 carbon atoms per molecule from at least one close-boiling alkane by extractive distillation of a feed consisting essentially of said at least one aromatic hydrocarbon and said at least one alkane, the improvement which comprises employing a solvent consisting essentially of a mixture of (a) N-(β-mercaptoethyl)-2-pyrrolidone and (b) cyclotetramethylene sulfone; wherein said extractive distillation process produces (i) an overhead distillate product which contains a smaller volume percentage of said at least one aromatic hydrocarbon and a larger volume percentage of said at least one alkane than said feed, and (ii) a bottoms product which contains said solvent and a larger volume percentage of said at least one aromatic hydrocarbon and a smaller volume percentage of said at least one alkane than said feed; and wherein said at least one aromatic hydrocarbon is separated from said solvent and recovered from said bottoms product.

2. A process in accordance with claim 1, wherein the weight ratio of component (b) to component (a) in said solvent is in the range of from about 0.2:1 to about 30:1.

3. A process in accordance with claim 1, wherein the weight ratio of component (b) to component (a) in said solvent is in the range of from about 1:1 to about 10:1.

4. A process in accordance with claim 1, wherein said at least one aromatic hydrocarbon in said feed is selected from the group consisting of benzene and toluene, and said at least one alkane in said feed contains 5-10 carbon atoms per molecule.

5. A process in accordance with claim 1, wherein said at least one aromatic hydrocarbon in said feed is toluene, and said at least one alkane is n-heptane.

6. A process in accordance with claim 1, wherein the weight ratio of said solvent to said feed is in the range of from about 0.5:1 to about 40:1.

7. A process in accordance with claim 6, wherein said weight ratio is in the range of from about 1:1 to about 10:1.

8. A process in accordance with claim 1, wherein said feed boils at a tempertaure in the range of from about 80° F. to about 350° F., at a pressure of about 1 atm.

9. A process in accordance with claim 1, wherein the boiling point of said at least one aromatic hydrocarbon and the boiling point of said at least one alkane differ from 0.2 to about 10° F., at a pressure of about 1 atm.

* * * * *

UNITED STATES PATENT AND TRADEMARK OFFICE
CERTIFICATE OF CORRECTION

PATENT NO. : 5,069,757

DATED : 12/03/91

INVENTOR(S) : Ronald E. Brown and Fu-Ming Lee

It is certified that error appears in the above-identified patent and that said Letters Patent is hereby corrected as shown below:

```
Title page, item [75], delete "," after "Brown" and insert
therefor --- ; Fu-Ming Lee, both of ---
```

Signed and Sealed this

Twenty-seventh Day of April, 1993

Attest:

MICHAEL K. KIRK

*Attesting Officer*     Acting Commissioner of Patents and Trademarks